United States Patent
Kuo

(10) Patent No.: US 8,738,394 B2
(45) Date of Patent: May 27, 2014

(54) CLINICAL DATA FILE

(76) Inventor: Eric E. Kuo, Foster City, CA (US)

(*) Notice: Subject to any disclaimer, the term of this patent is extended or adjusted under 35 U.S.C. 154(b) by 1153 days.

(21) Appl. No.: 11/983,280

(22) Filed: Nov. 8, 2007

(65) Prior Publication Data

US 2009/0125329 A1     May 14, 2009

(51) Int. Cl.
*G06Q 10/00* (2012.01)
*G06Q 50/00* (2012.01)
*G06Q 50/22* (2012.01)
*G06Q 50/24* (2012.01)

(52) U.S. Cl.
CPC ............. *G06Q 50/22* (2013.01); *G06Q 50/24* (2013.01)
USPC ................................ 705/2; 705/3

(58) Field of Classification Search
CPC ............................. G06Q 50/22; G06Q 50/24
USPC ....................................... 705/2–3
See application file for complete search history.

(56) References Cited

U.S. PATENT DOCUMENTS

| | | | |
|---|---|---|---|
| 6,018,713 A | 1/2000 | Coli et al. | |
| 6,523,009 B1 | 2/2003 | Wilkins | |
| 6,978,268 B2 | 12/2005 | Thomas et al. | |
| 7,016,952 B2 | 3/2006 | Mullen et al. | |
| 7,191,451 B2 | 3/2007 | Nakagawa | |
| 2001/0032100 A1* | 10/2001 | Mahmud et al. | 705/2 |
| 2002/0007284 A1 | 1/2002 | Schurenberg et al. | |
| 2004/0107118 A1* | 6/2004 | Harnsberger et al. | 705/2 |
| 2005/0144150 A1* | 6/2005 | Ramamurthy et al. | 706/45 |
| 2005/0216314 A1* | 9/2005 | Secor | 705/3 |
| 2006/0173715 A1 | 8/2006 | Wang | |
| 2006/0277075 A1 | 12/2006 | Salwan | |
| 2007/0192137 A1* | 8/2007 | Ombrellaro | 705/2 |
| 2008/0059238 A1* | 3/2008 | Park et al. | 705/3 |

OTHER PUBLICATIONS

Virtual Orthodontics. "Our Innovative Software". http://www.virtualorthodontics.com/innovativesoftware.html (2005).

* cited by examiner

*Primary Examiner* — Sheetal R Rangrej
(74) *Attorney, Agent, or Firm* — Brooks, Cameron & Huebsch, PLLC

(57) ABSTRACT

Clinical data file embodiments and methods for creating the same are provided. One embodiment includes treatment professional information in at least one of a number of treatment professional information data fields in a treatment professional section of the file, patient personal information in at least one of a number of patient personal information data fields in a patient profile section of the file, a number of patient medical information items, and an indicator associated with at least one of the treatment professional information data fields, at least one of the patient personal information data fields, and at least one of the patient medical information items, where the treatment professional information, patient personal information, and patient medical information items associated with an enabled indicator are hidden.

22 Claims, 4 Drawing Sheets

CLINICAL DATA FILE

BACKGROUND

The present disclosure relates to devices, files, mediums, and methods for keeping medical information private. The present disclosure, for example, includes a data file, where a treatment professional can designate as private, at least a portion of the medical or other information therein.

In some instances, it is beneficial when planning an orthodontic treatment process to confer and discuss various possible treatment routes with other treatment professionals (e.g., specialists such as orthodontists, oral surgeons, periodontists, and/or general dentists). However, although patient data can now be sent almost instantaneously over the Internet, it can be desirable to keep patient medical information as well as treatment professional information private (e.g., hidden) from a conferring treatment professional.

In addition, in determining a treatment process, information can be gathered in many different file formats. For example, information can include two and/or three-dimensional images, digital and/or analog images, and/or digital and/or analog video of a patient's mouth and/or surrounding features. Also, text files can be generated, including notes, comments, prescription notes, and/or medical history. However, difficulties can arise in viewing and sending multiple types of files since each type of file may require that each treatment professional have special software for each type of file.

DETAILED DESCRIPTION

According to the present disclosure, systems, devices, files, and methods are provided for converting clinical data to a single format and creating a clinical data file including the clinical data in the single format. Also, in some embodiments, treatment professional information, patient personal information, and/or patient images designated as private included in the clinical data file can be provided upon entering a pass code. As used herein, "clinical data" refers to data generated in the process of treating a patient. For example, clinical data can include, but is not limited to, patient medical information (e.g., dental or other medical information) items including x-rays, two and/or three-dimensional (3-D) models of a medical patient's mouth, and/or digital and/or analog pictures of the patient's teeth. In addition, clinical data can include prescription notes and/or treatment professional comments.

Clinical data can also include other information generated when forming a treatment plan for the patient. For example, such other information can include information that is generated in instances where the treatment plan is to reposition the patient's teeth with a number of stages of incrementally moving teeth using a plurality of discrete appliances, where each appliance successively moves one or more of the patient's teeth by incremental amounts.

In some embodiments, methods of the present disclosure can be carried out by instructions stored in memory and executed by a processor in a computing device. The instructions can, for example, be included in a computing device readable medium. In such embodiments, a computing device readable medium can be any medium that can store computing device readable information thereon. Suitable examples include optically or magnetically readable forms of media, among others.

Figure 1:
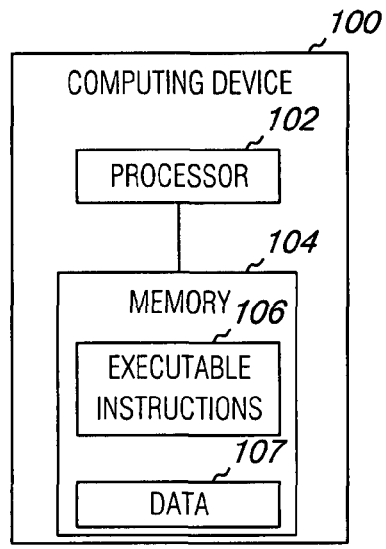
FIG. 1 illustrates a computing device embodiment to perform the methods of the present disclosure.

FIG. 1 illustrates a computing device embodiment to perform the methods of the present disclosure. In some embodiments, the computing device 100 can be used to create a clinical data file. In the computing device embodiment of FIG. 1, the device 100 includes one or more processors 102 in communication with one or more memory locations 104. The memory 104 can include a number of instructions 106 that can be executed on the processor 102. Memory 104 can also include one or more items of data 107 that can be used in the execution of the instructions 106 by the processor 102. The instructions 106 can, for example, be executed by the processor 102 to cause the computing device 100 to perform a method of the present disclosure, as described herein.

Figure 2:
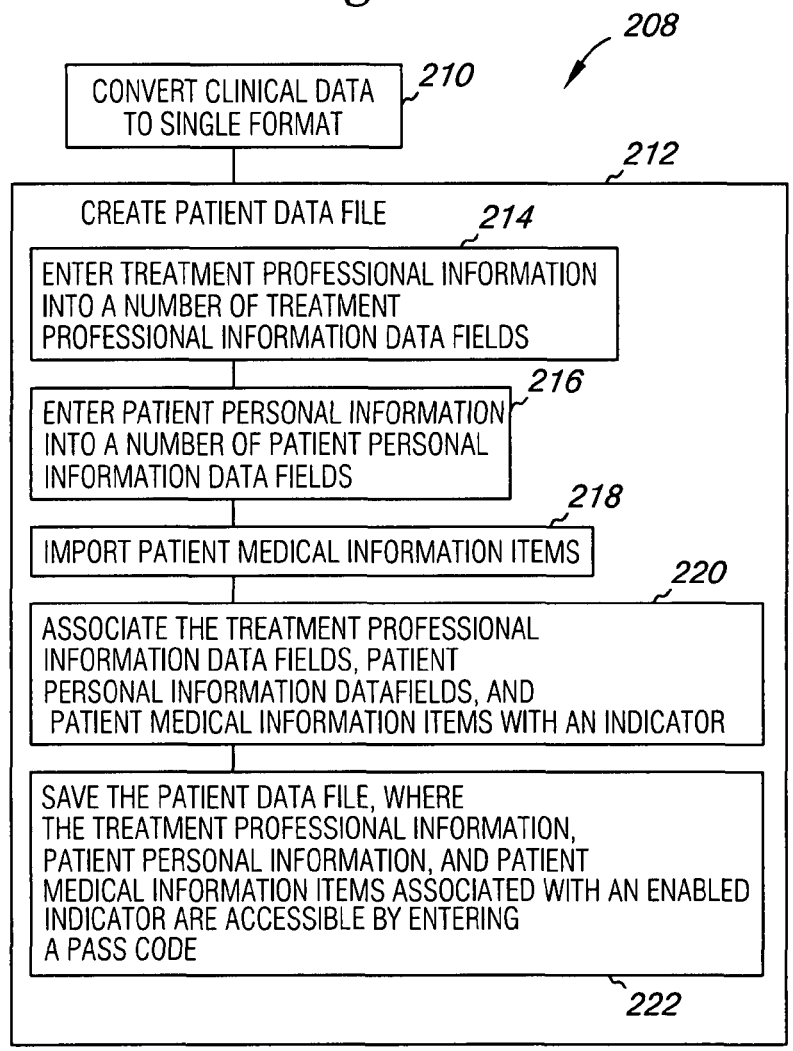
FIG. 2 illustrates a method for creating a clinical data file and securing medical information according to an embodiment of the present disclosure.

FIG. 2 illustrates a method for creating a clinical data file and securing medical information according to embodiments of the present disclosure. Unless explicitly stated, the method embodiments described herein are not constrained to a particular order or sequence. Additionally, some of the described method embodiments or elements thereof can occur or be performed at the same point in time.

As illustrated at block 210, the method 208 includes converting clinical data to a single format. In some embodiments, the conversion of clinical data can include converting all clinical data to a single format that is a different format than the clinical data is created in originally. For example, in some embodiments, the clinical data can be converted into a portable document format (PDF). In some embodiments, the conversion of clinical data can include converting a portion of the clinical data to a single format, where some clinical data is currently in the single format.

As illustrated at block 212, the method 208 includes creating a clinical data file 212 including the clinical data. As illustrated, creating the clinical data file 212 can include several steps.

For example, at block 214 treatment professional information can be entered into a number of treatment professional information data fields in a treatment professional profile section of the clinical data file. Treatment professional information can include, but is not limited to, treatment professional name, office address, office contact information (e.g., telephone number, fax number, electronic mail address), office logo, treatment professional photograph, practice mission/personal statement, and/or treatment professional resume highlights, among other items.

At block 216, patient personal information can be entered into a number of patient personal information data fields in a patient profile section of the clinical data file. The patient profile section can, for example, include, patient name, address, contact information (e.g., telephone number, fax number, electronic mail address), social security number, date of birth, gender, and/or insurance, among others.

At block 218, patient medical information items (e.g., patient images) can be imported into the clinical data file. In some embodiments, the patient medical information items can include several different types of patient images including x-ray, two or three-dimensional, and/or digital and/or analog images, among others.

In addition, in some instances, the various patient images may be created in many different file formats, making it difficult to view all of the patient images without specific software for each file format. By providing (e.g., converting) the clinical data (e.g., patient image) in a single format, and subsequently importing the patient images into the clinical data file, patient images that may have been created using different software can be viewed from the clinical data file using a single file viewer enabled by a single software application.

The many different types of patient images can include, for example, facial anterior (repose), facial anterior (smiling), profile (repose), profile (smiling), right buccal, left buccal, anterior intraoral, upper occlusal, lower occlusal, close-up smile, individual teeth, patient medical history (e.g., dental history), patient diagnosis, a three-dimensional (3-D) model of the patient's mouth (e.g., ClinCheck 3-D model, Invisalign® proprietary software that illustrates the movement of teeth), full mouth series x-rays, panoramic x-rays, cephalometric x-rays, and/or individual radiographs, among others. Since the patient images can include many different types of images, in some embodiments, creating the clinical data file 212 can include labeling the imported patient images according to data type (e.g., profile (smiling)).

In addition, in some embodiments, creating the clinical data file 212 can include positioning at least one patient image in a data file menu, as discussed further herein. For example, the patient images can be positioned in a hierarchy (e.g., a descending order) of importance according to a treatment professional. In some embodiments, instructions can be executed by the processor to put the imported images into a default position in the data file menu.

In some embodiments, at least one patient image can be represented by a thumbnail on the data file menu. In some such embodiments, instructions can be provided to select a thumbnail of a patient image which can initiate executable instructions to access an enlarged patient image and present the enlarged image on a display, among other functions.

As illustrated at block 220, creating the clinical data file 212 can include associating the treatment professional information data fields, patient personal information data fields, and/or patient medical information items with an indicator. The indicator functionality can be accomplished in various manners. For example, in some embodiments, the indicator can be a box that can be checked to enable the indicator.

In various embodiments, the indicator can be a drop down menu listing possible properties of the data field and/or information item. For example, the drop down menu properties can include, "hide information", "display information", and/or "secure information," among other suitable functions.

In such embodiments, when "hide information" is selected, the information contained in the data field and/or the information item, or portions thereof, can be hidden from a user viewing the clinical data file. When "display information" is selected, the information contained in the data field and/or the information item can be shown to the user viewing the clinical data file. When "secure information" is selected, the information contained in the data field and/or the information item can be shown by entering a pass code.

Also, as illustrated at block 222, the method 208 includes saving the clinical data file, where the treatment professional information, patient personal information, and/or patient medical information items associated with an enabled indicator can be accessed by entering a pass code.

In some embodiments, a method can include instructions executed by the processor to embed a pass code into the clinical data file once the clinical data file is saved in memory. For example, the pass code can be used to restrict viewing of some information (e.g., text/images, time based information, regions of images (e.g., eyes)), some files, and/or restrict transfer and/or modification of such information/files.

The pass code, for example, can be a password known to the user. The pass code can alternatively be an identifier associated with a computing device, such as an identifier uniquely associated with the computing device or network when the clinical data file is saved.

Further, a method can include instructions that are executed by the processor to allow the clinical data file to be modified after the pass code is entered into the computing device. By embedding a pass code into the clinical data file and preventing modifications to the clinical data file without the pass code, the clinical data file can be viewed by a limited number of users, however, only authorized users can modify the clinical data file. In addition, limiting modification ability can help to maintain the authenticity and integrity of the clinical data file.

In some embodiments, multiple pass codes can be used, where one pass code can allow modifications to the clinical data file and a second pass code can allow the ability to view the clinical data file without the ability to modify. Other pass codes can also be created to allow the viewing of specific items and/or areas of the clinical data file.

Once the clinical data file has been created and saved, instructions can be executed by the processor to view the clinical data file on a display. Viewing the clinical data file can include viewing the data file menu, the patient profile, and/or the treatment professional profile, among other things, as discussed herein.

Figure 3:
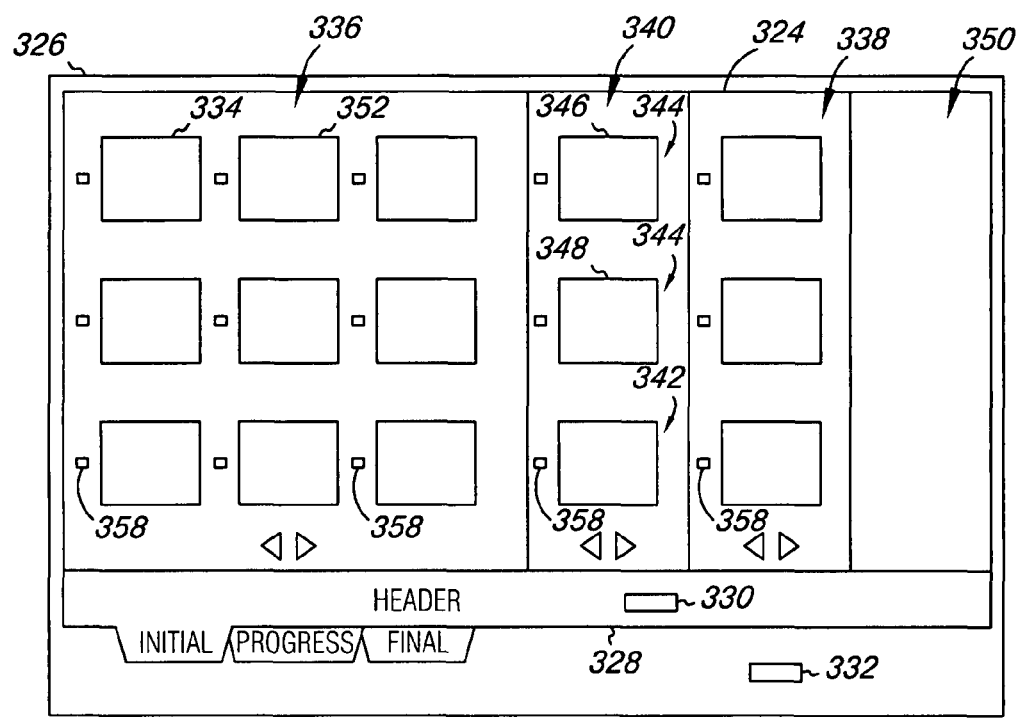
FIG. 3 is an illustration of a data file menu on a display according to an embodiment of the present disclosure.

FIG. 3 is an illustration of a data file menu 324 on a display 326 according to embodiments of the present disclosure. The data file menu 324 can include a header 328 displaying various patient personal information, such as a patient's name and age, among other items. For example, in some embodiments, the header 328 can display a patient's initials to maintain a patient's privacy, as discussed herein.

The header 328 can also include a patient personal information icon 330. When the patient personal information icon 330 is selected, instructions can be executed by the processor to view the patient profile section, as discussed herein.

In addition, the data file menu 324 can include a treatment professional information icon 332. Similarly, when the treatment professional icon 332 is selected, instructions can be executed by the processor to view the treatment professional profile section, as discussed herein.

In some embodiments, the patient images 334 can be separated into sections on the data file menu 324. For example, as shown in FIG. 3, patient images 334 that are photographs can be in a photograph section 336, patient images 334 that are x-rays can be in an x-ray section 338, and a third section 340 can include 3-D models 342 and text information 344.

In some embodiments, the text information 344 can be free text 346. In addition, as discussed herein, patient images 334 can include patient medical history. In some embodiments, the patient medical history can be a text image 348. In addition, in some embodiments, the data file menu 324 can include a comment section 350.

As discussed herein, in some embodiments, at least one patient image 334 can be associated with a thumbnail 352. As shown in FIG. 3, the data file menu 324 can include thumbnails 352 of the patient images 334 so that more images can be seen at one time.

In addition, when the patient image 334 is originally imported into the clinical data file, the patient image 334 and/or thumbnail 352 can be associated with an indicator 358. In some embodiments, the indicator 358 can be a box, as shown in FIG. 3, where the box can be "checked" to enable the indicator 358 when enabled executable instructions can be initiated to perform a function having to do with the image.

In some such embodiments, when an indicator 358 is enabled, instructions executable by the processor can hide the image 334 associated with the enabled indicator 358 when the clinical data file is being viewed by a user, as discussed herein. Therefore, when a user views the clinical data file, the user can see the data file menu 324 as illustrated in FIG. 3, without the indicators 358.

Figure 4:
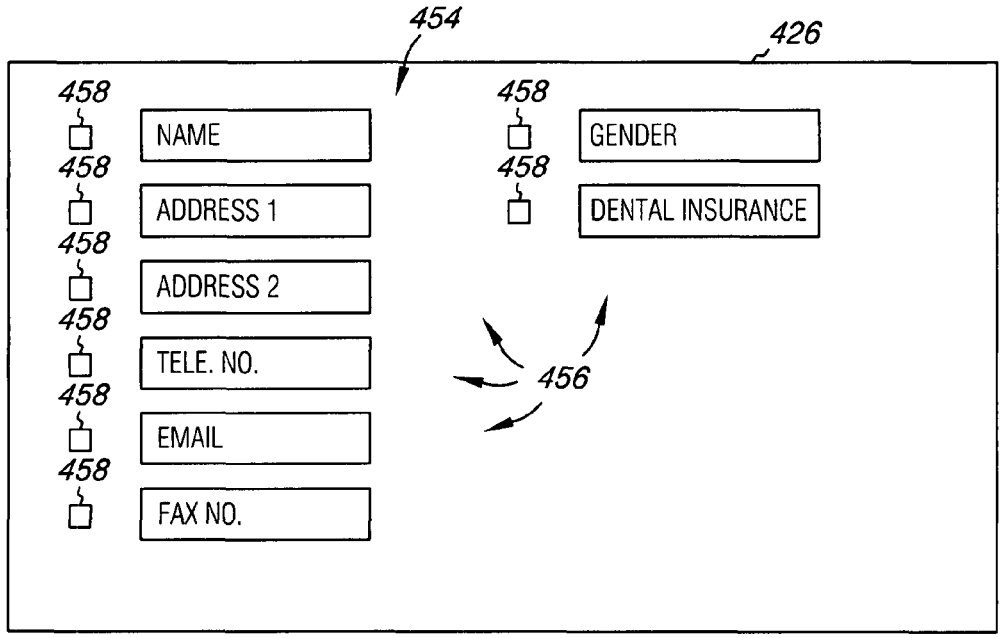
FIG. 4 is an illustration of a display of a patient profile section according to an embodiment of the present disclosure.

FIG. 4 is an illustration of a display 426 of a patient profile section 454 according to embodiments of the present disclosure. The patient profile section 454 illustrated shows the section 454 when the clinical data file is created.

In FIG. 4, the patient profile section 454 can include various data fields 456 that can be filled in with different types of information including, for example, name, address, telephone number, email, fax number, gender, and/or insurance, among others. When the patient personal information icon on the data file menu is selected by a user, other than the user (e.g., treatment professional) creating the clinical data file, the patient profile section 454 can be as illustrated without the indicators, as discussed herein.

Each patient personal data information data field 456 can be associated with an indicator 458. Similarly to the indicators 358 of FIG. 3, the indicators 458 can be of any suitable type. In some embodiments, the indicator 458 can be a box, as shown in FIG. 4, where the box can be "checked" to enable the indicator 458.

In such embodiments, when an indicator 458 is enabled, instructions executable by the processor can hide the information associated with the enabled indicator 458 when the clinical data file is being viewed by a user, as discussed herein. For example, when the indicator 458 associated with the patient's name is enabled, the patient's name can be hidden, and the patient's initials can be displayed in the data file menu, as discussed herein.

In some embodiments, the information associated with the enabled indicator 458 can be shown by entering a pass code, as discussed herein. In addition, in various embodiments, the indicator 458 can be a drop-down menu, where a user can select either "hide information," "display information," or "secure information" for each patient personal information data field 456.

In some embodiments, when a user selects the patient personal information icon on the data file menu, the patient profile can be displayed (e.g., as shown in FIG. 4 without the indicators 458), and the data fields associated with enabled indicators 458 can be displayed with, for example, the message "confidential information." In addition, data fields that are left blank when the clinical data file is created can be absent from the patient profile section 454. By distinguishing between a data field containing confidential information and a data field that is blank, a treatment professional can determine whether it would be useful to obtain permission to view the confidential information, rather than obtain permission to view confidential information only to find the data field blank.

Figure 5:
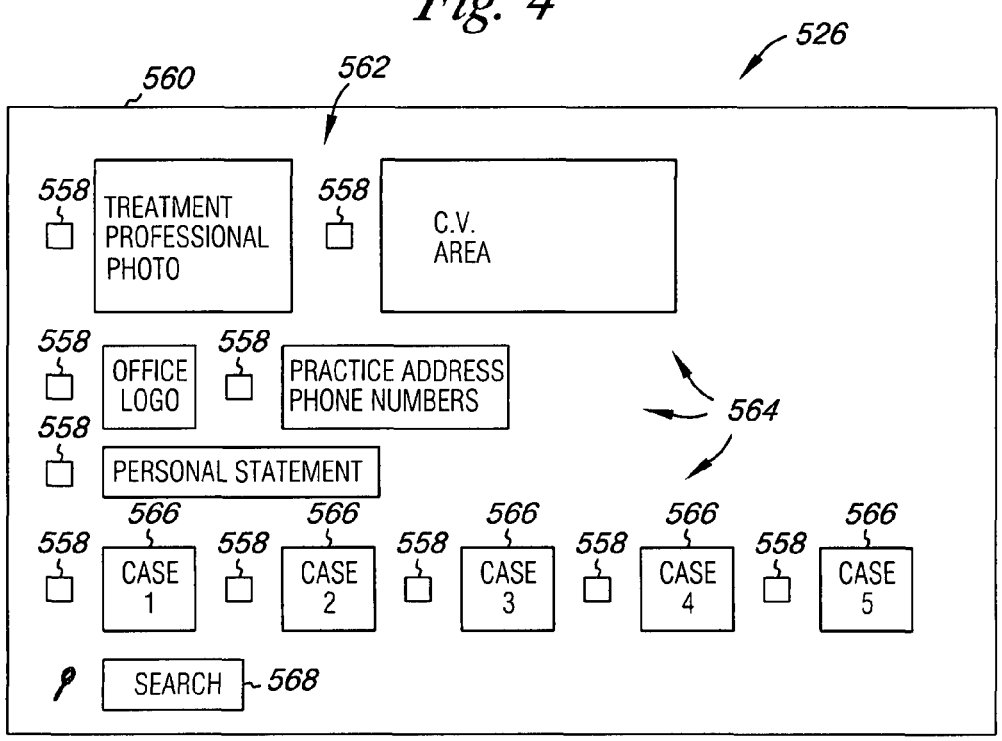
FIG. 5 is an illustration of a display of a treatment professional profile section according to an embodiment of the present disclosure.

FIG. 5 is an illustration of a display 526 of a treatment professional profile section 560 according to embodiments of the present disclosure. Similarly to the patient profile section (e.g., FIG. 4), the treatment professional profile section 560 illustrated shows the treatment professional profile section 560 when the clinical data file is created.

As discussed herein, when the treatment professional icon is selected, instructions can be executed by the processor to view the treatment professional profile section 560. The treatment professional profile section 562 can include various treatment professional data fields 564 that can be filled in with different types of information including, for example, a treatment professional photograph, a practice address and phone number, an office logo, a personal statement, consulting rates, and/or resume highlights, among others.

In some embodiments, the treatment professional profile section 562 can include sample cases 566 for a potential patient to view. The potential patient can select a sample case 566, where instructions executable by the processor can display a data file menu (e.g., FIG. 3), and the potential patient can see "before" and "after" images of, for example, a patient's teeth. The potential patient can then determine if the treatment professional is a good match for the particular treatment that the potential patient requires based on the sample cases 566.

In such embodiments, the clinical data file can include multiple treatment professional profiles including several sample cases 566. In addition, in some embodiments, the treatment professional profile section 562 can include a search tool 568. In such embodiments, the potential patient can enter a search term into the search tool 568, and instructions executable by the processor can display treatment professional profile sections 562 that include the search term.

In some embodiments, the treatment professional profile section 562 can include a rating indicating how much experience the treatment professional has with a certain treatment option. For example, the rating can indicate how much experience the treatment professional has with using technologies from Align Technology, Inc.

In addition, as discussed herein, in some embodiments, the treatment professional profile section 562 can include a data field 564 where the treatment professional can enter consulting rates. This information can be useful for a potential patient when selecting a treatment professional and/or a treatment professional seeking a second opinion.

In addition, the treatment professional can keep identifying information about the patients in the sample cases 566 private by enabling the indicators 558 associated with patient personal information data fields in the patient profile section, as discussed herein. Each treatment professional data field 564 can be associated with an indicator 558, as discussed herein with regard to the patient profile section (e.g., FIG. 4). When an indicator 558 is enabled, instructions executable by the processor can hide the information associated with the enabled indicator 558 when the clinical data file is being viewed by a user, as discussed herein.

In some embodiments, the information associated with the enabled indicator 558 can be shown by entering a pass code, as discussed herein. In addition, in various embodiments, the indicator 558 can be a drop-down menu, where a user can select either "hide information," "display information," or "secure information" for each treatment professional information data field 564.

In various embodiments, treatment professional information entered into data fields 564 associated with a disabled indicator 558 can be embedded into the clinical data file. In such embodiments, the treatment professional information can be unmodifiable except by the treatment professional, for example, by entering a pass code.

In some embodiments, when a user selects the treatment professional icon is selected on the data file menu, the treatment professional profile can be displayed (e.g., as shown in FIG. 5 without the indicators 558), and the data fields associated with enabled indicators 558 can be displayed with, for example, the message "confidential information." In addition, data fields that are left blank when the clinical data file is created can be absent from the treatment professional profile section 562, as discussed herein.

As discussed herein, when viewing the data file menu (e.g., FIG. 3), one or more patient images can be shown as a thumbnail. In addition, the thumbnail can be selected and instructions can be executable by the processor to enlarge the patient image.

Figure 6:
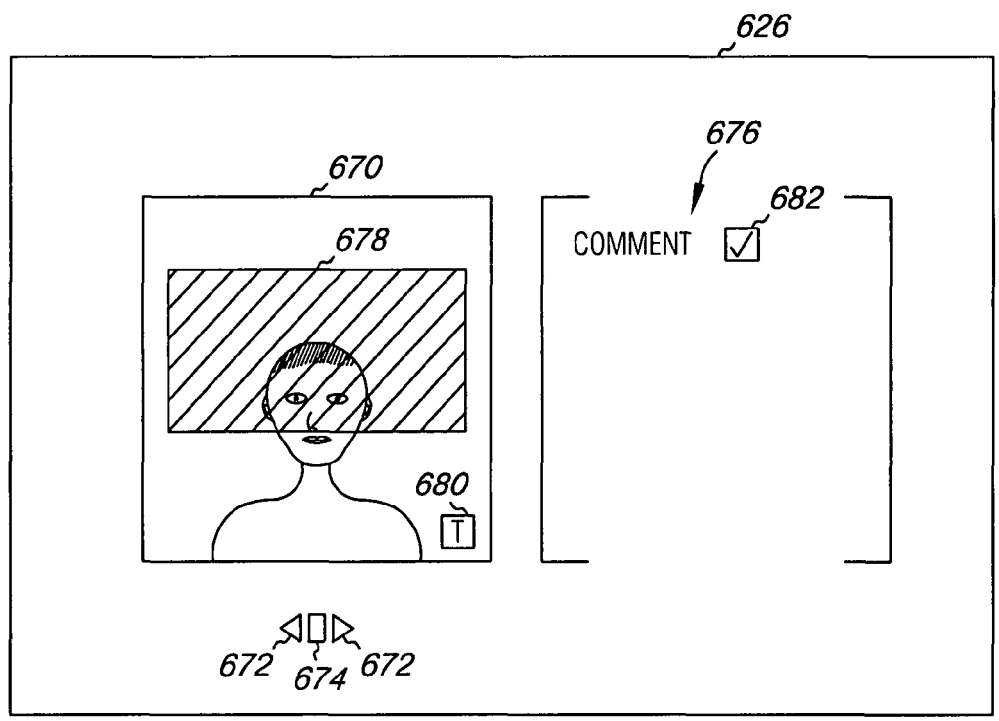
FIG. 6 is an illustration of a display of an enlarged patient image according to an embodiment of the present disclosure.

FIG. 6 is an illustration of a display 626 of an enlarged patient image 670 according to embodiments of the present disclosure. In some embodiments, the display 626 can include navigation arrows 672, where instructions can be executed by the processor to advance the enlarged patient image 670 from one image to the next patient image in the data file menu.

Instructions can also be executed to go back to the previous patient image in the data file menu when one of the navigation arrows 672 is selected. The display can also include a menu shortcut 674, where instructions can be executed by the processor to return to the data file menu (e.g., FIG. 3) when selected.

As illustrated in FIG. 6, the display of the enlarged patient image 670 can include a comments section 676 as discussed herein. In some embodiments, when the thumbnail of a patient image is selected, instructions can be executed by a processor to enlarge the patient image, as shown in FIG. 6, and to display comments associated with the patient image in the comment section 676.

In some embodiments, a patient image can include notations on the image. In some embodiments, a comment in the comment section 676 can explain the notation on the image.

In some embodiments, when the clinical data file is created and the patient images are imported, a user (e.g., treatment professional) can modify the patient image in various manners. For example, in some embodiments, modification can be accomplished by highlighting an area, by circling an aspect and/or area, and/or by including a privacy region 678. Such actions can be accomplished by executable instructions to perform and display such modifications.

FIG. 6 illustrates the privacy region 678 where an area of the enlarged patient image 670 is blacked out. Blacking out an area of a patient image can help a treatment professional hide identifying characteristics of a patient.

In some embodiments, the privacy region 678 can include an area of the patient image that is, for example, blurred rather than blacked out. In some embodiments, the privacy region 678 can be accessible by entering a pass code.

Including the privacy region 678 can allow a treatment professional to provide the clinical data file to a potential patient or to send the clinical data file to a second treatment professional for a second opinion without losing doctor-patient confidentiality. It can also allow the treatment professional to send the clinical data file over an unsecured internet connection (e.g., public email) while retaining the anonymity of the patient information included in the clinical data file. Including the privacy region 678 can also decrease the need for additional documentation between the treatment professional, patient, and second treatment professional regarding permission to view the clinical data file. In some embodiments, the user can include a comment in the comment section 452 explaining the modification and/or privacy region 678.

In some embodiments, the data file menu comment section (e.g., comment section 350 in FIG. 3) can include a list of comments such as comments regarding modifications to images and comments made by a treatment professional when creating and/or viewing the clinical data file, as discussed herein. In some embodiments, the comment section illustrated in FIG. 6 can include the list of comments displayed in the comment section on the data file menu.

In various embodiments, the comment section illustrated in FIG. 6 can include just the one or more comments associated with the enlarged patient image 670, as discussed herein. In some embodiments, the user can choose between viewing the entire list of comments from the data file menu or the comments associated with the enlarged patient image 670, or can select comments to be viewed.

As shown in FIG. 6, the enlarged patient image 670 can include a toolbar 680 for modifying the enlarged patient image 670. When the toolbar 680 is selected, instructions executed by the processor can cause tools to appear, such as, text tools, fill tools, and/or draw tools, including circle, square, pen size selection, and/or color selection, among others.

An exit tool can also appear when the toolbar 680 is selected, in some embodiments. In such embodiments, once the tools appear, a user can modify the enlarged patient image 670 to highlight an area of interest and/or to make a notation on the enlarged patient image 670, among other modifications.

Once the user is finished, the user can select the exit tool and instructions executable by the processor can save the modifications. In addition, the user can enter comments into the comment section 676, as discussed herein, explaining the modifications and/or inquiring about a portion of the enlarged patient image 670.

Other types of comments can also be entered into the comment section 676. For example, in some embodiments, instructions executable by the processor can save the modifications and/or the comments entered into the comment section 676 separate from the enlarged patient image 670. In addition, by entering comments into the comment section 676 with the enlarged patient image 670, instructions executed by the processor can associate the comments with the enlarged patient image 670 displayed when the one or more comments are entered.

As discussed herein, in some embodiments, the comments entered into the comment section 676 with the enlarged patient image 670 can also be seen on the data file menu in the comment section as a discussion thread. In embodiments where the comments entered are associated with the enlarged patient image 670 displayed when the comment is entered, a tag 682 can be inserted into the comment section 676 with the enlarged patient image 670 as well as next to the comment in the comment section on the data file menu.

As used herein, the tag 682 refers to an icon, where the icon can be a graphic picture (e.g., a pencil), and/or a textual hyperlink. In such embodiments, instructions can be executed by a processor to enlarge the modified patient image associated with the comment when the tag 682 is selected. In some embodiments, more than one modified patient image can be enlarged when multiple tags 682 are selected.

As discussed herein, in some embodiments, a treatment professional can send the clinical data file to a second treatment professional for a second opinion. In some embodiments, the second treatment professional can modify the enlarged patient images 670 and/or insert comments.

In such embodiments, by associating a tag with a comment when the comment is inserted after the enlarged patient image 670 is modified, the treatment professional can view the enlarged patient images 670 directly from the data file menu by selecting the tag 682 associated with the comment. This can help the treatment professional follow the order in which the second treatment professional viewed the clinical data file, facilitating greater understanding of the second opinion and the thought process to form the second opinion.

In some embodiments, once the user is finished modifying the enlarged patient image 670 and/or entering comments into the comment section 676 and selects the exit tool, instructions can be executed by the processor to secure the comments and/or modifications from further modification. In some embodiments, the comments and/or modifications can be modified after entering a pass code into the computing device.

In some embodiments, instructions are executed by the processor to send the clinical data file to a second computing device. In various embodiments, the clinical data file can be sent to a second user, as discussed herein, where the user can view the clinical data file on the same computing device, a second computing device, or an unnetworked computing device by transport of one or more files on a portable computing device readable medium.

For example, the clinical data file can be sent from a first treatment professional to a second treatment professional via the Internet. The second treatment professional can then open and view the clinical data file on a display at any computing device that includes a computing device readable medium having instructions which can be executed by a processor to cause a computing device to view the clinical data file.

In some embodiments, once the clinical data file is received, instructions which can be executed by a processor can cause the computing device to view the clinical data file menu (e.g., as shown in FIG. 3), on a display 626. The clinical data file menu can include, for example, one or more thumbnails of patient images, one or more tabs in a sequence of tabs, one or more comment sections, patient personal information, and/or treatment professional information, as discussed herein. In addition, a thumbnail can be selected to enlarge the patient image.

In such embodiments, the treatment professional or other user who receives the clinical data file can use the tool bar 680 to modify one or more enlarged patient images 670, and/or can enter comments into the comment section 676. As discussed herein, a tag 682 can be inserted in the comment section 676 when the comment is associated with the enlarged patient image 670 that is modified and/or that is displayed when the comment is entered. The treatment professional or other user can repeat this process for as many patient images as desired.

As discussed herein, the modifications and comments can be saved separately from the enlarged patient images 670. In such embodiments, the treatment professional, or other user, can send the modifications and comments to the computing device that the clinical data file was received from and/or to another computing device or save to a fixed or portable computing device readable medium. When the original computing device and/or different computing device receives the modifications and/or comments, instructions can be executed by the processor to allow the receiving user to accept or reject the modifications and/or comments.

In embodiments where the receiving computing device includes the clinical data file, accepting the modifications and/or comments can cause instructions executed by the processor to save the modifications and/or comments and merge them with the clinical data file. In embodiments where the receiving computing device does not include the clinical data file, accepting the modifications and/or comments can cause instructions executed by the processor to save the modifications and/or comments as well as the entire clinical data file. In some embodiments, the user sending the modifications and/or comments can choose whether to send the modifications, comments, and/or the entire clinical data file.

By saving the modifications and/or comments separately from the enlarged patient images 670, the enlarged patient image 670 as well as the clinical data file can be maintained in the form in which it was created. This can help to prevent unintended and/or unauthorized modifications to the clinical data file.

Allowing the user to accept or reject modifications and/or comments can also help to prevent unauthorized modifications. In addition, saving the modifications and/or comments separately from the enlarged patient images 670 can preserve the original, unaltered patient image, which may be important for medico-legal documentation purposes.

In some embodiments, the modifications and/or comments can be saved separately from the enlarged patient images 670 and arranged as layers on the enlarged patient images 670. In such embodiments, the layers of modifications can be removed (e.g., by entering one or more pass codes) to revert to the original, unaltered patient image and other information. In other words, the enlarged patient images 670 and modifications and/or comments can be viewed separately, in some cases, by entering a pass code.

In some embodiments, more than one treatment professional, or other user, can send modifications and/or comments to the original treatment professional. In such embodiments, when the modifications and/or comments are accepted, instructions executed by the processor can cause more than one set of modifications and/or comments to be merged with the clinical data file.

In such embodiments, the different sets of modifications and/or comments can be displayed with an identifier to indicate the sender. For example, each treatment professional, or other user, sending modifications and/or comments can be assigned a different color, identifier, and/or font.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A clinical data file for medical information, comprising:
    treatment professional information, provided by a first treatment professional that controls the clinical data file, in at least one of a number of treatment professional information data fields in a treatment professional profile section of the file;
    patient personal information, provided by a patient or the first treatment professional, in at least one of a number of patient personal information data fields in a patient profile section of the file;
    a number of patient medical information items, provided by the patient or first treatment professional, wherein at least one of the number of patient medical information items comprises an image of the patient including a privacy region, where the privacy region hides a first area of the image and leaves a second area of the image visible, and wherein the hidden first area is accessible by a pass code; and
    an indicator associated with at least one of the treatment professional information data fields, at least one of the patient personal information data fields, and at least one of the patient medical information items, where the indicator has an enabled state and a disabled state and where the at least one of the treatment professional information, patient personal information, and patient medical information items associated with the indicator are hidden when the first treatment professional selects the enabled state for the indicator and the clinical data file is viewed by a second treatment professional.

2. The clinical data file of claim 1, where the treatment professional information, patient personal information, and patient medical information items associated with the enabled indicator are accessible via the pass code, wherein the pass code includes an embedded pass code included in the clinical data file.

3. The clinical data file of claim 1, where the privacy region is one of blacked out and blurred, and where the privacy region hides identifying characteristics of the patient.

4. The clinical data file of claim 3, where the privacy region is accessible by entering the pass code.

5. The clinical data file of claim 1, where the clinical data file includes text information.

6. The clinical data file of claim 1, where the clinical data file includes dental notations.

7. The clinical data file of claim 1, where the clinical data file includes a data file menu with one or more thumbnails of the patient medical information items.

8. A computing device readable medium having executable instructions which can be executed by a processor to cause a computing device to perform a method, comprising:
    converting clinical data to a single format;
    creating a clinical data file, controlled by a first treatment professional, including the clinical data in the single format, where creating the clinical data file includes:
        entering treatment professional information into a number of treatment professional information data fields in a treatment professional profile section;
        entering patient personal information into a number of patient personal information data fields in a patient profile section;
        importing a number of patient medical information items into the clinical data file, wherein at least one of the number of patient medical information items comprises an image of the patient including a privacy region, where the privacy region hides a first area of the image and leaves a second area of the image visible, and wherein the hidden first area is accessible by a pass code;
        associating the at least one of the treatment professional information data fields with a first indicator, where the first treatment professional enables the first indicator to hide at least one of the number of treatment professional information data fields when the clinical data file is viewed by a second treatment professional;
        associating at least one of the patient personal information data fields with a second indicator, where the first treatment professional enables the second indicator to hide at least one of the number of patient personal information data fields when the clinical data file is viewed by a second treatment professional;
        associating at least one of the patient medical information items with a third indicator, where the first treatment professional enables the third indicator to hide at least one of the number of patient medical information items when the clinical data file is viewed by a second treatment professional; and
        saving the clinical data file, where the treatment professional information, patient personal information, and patient medical information items associated with an enabled indicator are accessible by the second treatment professional by entering the pass code.

9. The medium of claim 8, where the method includes embedding the treatment professional information associated with a disabled indicator in the clinical data file.

10. The medium of claim 8, where the pass code is embedded in the clinical data file.

11. The medium of claim 8, where the clinical data file is modifiable via the pass code.

12. The medium of claim 8, where creating the clinical data file further includes labeling the imported patient images according to a data type and organizing the patient images according to the data type.

13. The medium of claim 8, where the privacy region is one of blacked out and blurred, and where the privacy region hides identifying characteristics of the patient.

14. The medium of claim 13, where the privacy region is accessible by entering the pass code.

15. The medium of claim 8, where the method includes adding non-image information including at least one of text information and dental notations.

16. A computing device comprising:
    a processor
    a memory connected to the processor; and
    computer executable instructions storable in the memory and executable by the processor to perform a method including:
        converting clinical data to a single format to create a clinical data file;
        entering treatment professional information into a number of treatment professional information data fields in a treatment professional profile section of a clinical data file;

entering patient personal information into a number of patient personal information data fields in a patient profile section of the clinical data file;

importing a number of patient images into the clinical data file, where at least one of the number of patient images includes a privacy region, and where the privacy region hides a first area of the image and leaves a second area of the image visible, and wherein the hidden first area is accessible by a pass code; and associating one or more of the treatment professional information data fields with a first indicator, where a first treatment professional enables the first indicator to hide at least one of the number of treatment professional information data fields when the clinical data file is viewed by a second treatment professional;

associating one or more of the patient personal information data fields and one or more of the patient images with a second indicator, where the first treatment professional enables the second indicator to hide at least one of the number of patient personal information data fields when the clinical data file is viewed by a second treatment professional;

associating the number of patient images with a third indicator, where the first treatment professional enables the third indicator to hide at least one of the number of patient images when the clinical data file is viewed by a second treatment professional; and saving the clinical data file, where the treatment professional information, patient personal information, and patient images associated with an enabled indicator are hidden when the clinical data file is viewed by a second treatment professional.

17. The computing device of claim 16, where the method includes sending the clinical data file to a second computing device, where the treatment professional information, patient personal information, and patient images associated with an enabled indicator are accessible by entering the pass code.

18. The computing device of claim 16, where the method includes modifying at least one of the number of the patient images.

19. The computing device of claim 18, where the method includes saving one or more of the modifications to the at least one patient image separate from the number of patient images.

20. The computing device of claim 19, where the method includes viewing at least one of the patient images or at least one of the modifications to the patient images separately after entering the pass code.

21. The computing device of claim 18, where the privacy region of the patient image is one of blacked out and blurred, and where the privacy region hides identifying characteristics of the patient.

22. The computing device of claim 21, where the privacy region is accessible by entering the pass code.

* * * * *